US012797543B2

(12) United States Patent
Boström

(10) Patent No.: US 12,797,543 B2
(45) Date of Patent: Nov. 17, 2026

(54) TRANSPORT LOCK ASSEMBLY FOR A MEDICAMENT DELIVERY DEVICE

(71) Applicant: SHL MEDICAL AG, Zug (CH)

(72) Inventor: Anders Boström, Ingaro (SE)

(73) Assignee: SHL Medical AG, Zug (CH)

( * ) Notice: Subject to any disclaimer, the term of this patent is extended or adjusted under 35 U.S.C. 154(b) by 630 days.

(21) Appl. No.: 18/221,025

(22) Filed: Jul. 12, 2023

(65) Prior Publication Data

US 2024/0033430 A1 Feb. 1, 2024

Related U.S. Application Data

(60) Provisional application No. 63/393,294, filed on Jul. 29, 2022.

(51) Int. Cl.
*A61M 5/20* (2006.01)

(52) U.S. Cl.
CPC ....... *A61M 5/20* (2013.01); *A61M 2005/2073* (2013.01); *A61M 2207/00* (2013.01)

(58) Field of Classification Search
CPC ............ A61M 5/20; A61M 2005/2073; A61M 2207/00
See application file for complete search history.

(56) References Cited

U.S. PATENT DOCUMENTS

2020/0164138 A1* 5/2020 Holmqvist .............. A61M 5/24

FOREIGN PATENT DOCUMENTS

WO 2014/154491 A1 10/2014
WO 2016/169748 A1 10/2016

* cited by examiner

*Primary Examiner* — Dung T Ulsh
(74) *Attorney, Agent, or Firm* — McDonnell Boehnen Hulbert & Berghoff LLP

(57) ABSTRACT

A transport lock assembly included in a sub-assembly for a medicament delivery device is disclosed that includes a powerpack having a locking member configured to interact with a control member, where the locking member is movable relative to the control member and a body of the power pack from a locked state in which the control member is immobilized, to an unlocked state in which the control member is free to move. The locking member can be moved from the locked to the unlock state by interaction with a needle guar or with an inner surface feature of housing into which the sub-assembly is inserted during the final assembly of the medicament delivery device.

20 Claims, 11 Drawing Sheets

TRANSPORT LOCK ASSEMBLY FOR A MEDICAMENT DELIVERY DEVICE

CROSS REFERENCE TO RELATED APPLICATIONS

The present application is a claims priority to U.S. Provisional Patent Application No. 63/393,294 filed Jul. 29, 2022 which is herewith incorporated by reference into the present application.

TECHNICAL FIELD

The present disclosure relates to a transport lock assembly for a medicament delivery device to prevent premature activation of the delivery device. More particularly, the present disclosure is directed to transport lock assemblies that prevent the powerpack component of a medicament delivery device from unintended activation prior to full assembly of the delivery device.

BACKGROUND

The disclosure relates to medicament delivery devices that are delivered as sub-assemblies for final assembly into, for instance, auto-injectors. One of the sub-assemblies may be a powerpack, which may comprise a pre-tensioned plunger rod, arranged with a control member that is configured to release the pre-tensioned plunger rod when the fully assembled medicament delivery device is used to deliver a medicament. For this reason, the control member is configured as a movable component, so that another component, typically comprised in a different sub-assembly, may interact with control member when the user of the medicament delivery device intends to administer a dose of medicament. The various sub-assemblies that comprise the fully assembled device can be prefabricated (pre-assembled) in more than one location and then transported to a final assembly location. During transport of the sub-assemblies, vibrations, movements and impacts may lead to accidental release of the pre-tensioned plunger rods, causing the powerpacks to prematurely fire, i.e., activate prior to the final assembly of the device. This results in a waste of components and represents a loss of time and money to the device manufacturer. It is therefore necessary to ensure that the control members are held securely so that they do not accidentally activate the powerpacks. At the same time, the locked powerpacks must not become difficult or complicated to unlock and/or to assemble with other device components during final assembly of the device because of the security measures taken relating to the control members.

Some attempts have been made to solve these problems, for example, U.S. Pub. 2020/0164138 and WO2014/154491, which discloses a transport lock mechanism for a powerpack where an actuator sleeve is prevented from axial movement during transportation. During assembly, a key member, arranged on an inner surface of a housing, interacts with the lock mechanism to rotate the actuator sleeve into a position in which it may move axially after assembly. In the present disclosure, the control member is rotationally locked. Therefore, a different mechanism is needed.

WO2016/169748, on the other hand, relates to a transport lock where a powerpack comprises a rotatable coupling member which controls the release of a biased plunger rod. During transportation, the coupling member is prevented from rotation by radially flexible tabs, such that when the power pack is assembled with a housing, the tabs are pushed radially inwards to free the coupling member for rotation in the assembled medicament delivery device. Due to tolerances, the unlocking of the coupling member during assembly is not always successful, which may lead to malfunctioning medicament delivery devices.

SUMMARY

In the present disclosure, when the term “distal” is used, this refers to the direction pointing away from the dose delivery site. When the term “distal part/end” is used, this refers to the part/end of the delivery device, or the parts/ends of the members thereof, which under use of the medicament delivery device is/are located furthest away from the dose delivery site. Correspondingly, when the term “proximal” is used, this refers to the direction pointing to the dose delivery site. When the term “proximal part/end” is used, this refers to the part/end of the delivery device, or the parts/ends of the members thereof, which under use of the medicament delivery device is/are located closest to the dose delivery site.

Further, the term “longitudinal”, with or without “axis”, refers to a direction or an axis through the device or components thereof in the direction of the longest extension of the device or the component.

The term “lateral”, with or without “axis”, refers to a direction or an axis through the device or components thereof in the direction of the broadest extension of the device or the component. “Lateral” may also refer to a position to the side of a “longitudinally” elongated body.

In a similar manner, the terms “radial” or “transversal”, with or without “axis”, refers to a direction or an axis through the device or components thereof in a direction generally perpendicular to the longitudinal direction, e.g. “radially outward” would refer to a direction pointing away from the longitudinal axis.

Also, if nothing else is stated, in the following description wherein the mechanical structure of the device and the mechanical interconnection of its components is described, the device is in an initial non-activated or non-operated state.

In view of the foregoing, a general object of the present disclosure is to provide a transport lock assembly for a powerpack of a medicament delivery device that prevents premature activation prior to the final assembly of the medicament delivery device.

According to a main aspect of the present disclosure there is provided a transport lock assembly for a powerpack of a medicament delivery device, wherein the transport lock assembly comprises a powerpack having a spring-biased drive member, a body for holding the spring-biased drive member in a pre-tensioned state, a control member for releasing the spring-biased drive member from the body, and a locking member configured to interact with the control member, which locking member is movable, relative to the control member, from a first state in which the control member is immobilized, to a second state in which the control member is free to move, the transport lock assembly being further characterized by an outer housing that slidably accepts a medicament delivery member guard and may include a key member, which housing part or housing is configured to receive sub-assemblies containing the delivery member guard and the powerpack during device assembly. In one embodiment, the delivery member guard during assembly may operatively move the locking member so that the control member is no longer immobilized. In another embodiment, the introduction of the power pack sub-assembly into the housing causes the key member to operatively engage the locking member so that the control member is no longer immobilized. In both embodiments the assembly process causes the locking member to move from a locked state to an unlocked state relative to the control member.

Preferably, when the locking member is in the locked state, the control member is in direct engagement with the locking member such that the control member is prevented from moving relative to the housing, more preferably the control member is prevented from rotating relative to the housing. Disengagement of the locking member from the control member occurs when the locking member moves to the unlocked state, wherein the control member is free to move, preferably rotate, relative to the housing, the body and the spring-biased drive member.

Accordingly, one possible embodiment of the medicament delivery device of the present disclosure has a housing having an open terminal distal end with a distally facing surface and a body locatable in the housing and having a first axial position and a second axial position, both relative to the terminal distal end of the housing. A control member is rotatably positioned on and axially fixed relative to the body and has a distal end with a first mating member. A locking member is rotatably fixed relative to the body and has a proximal end containing a second mating member configured to engage with the first mating member when the locking member is in a locked state. The distal end of the locking member has a tab. When the body is in the first axial position, the first and second mating members are engaged such that rotation of the control member relative to the body is prevented, and when the body is moved to the second axial position, the tab engages with the distally facing surface of the housing to cause the first and second mating members to disengage and the locking member to be in an unlocked state in which the control member is free to rotate relative to the tubular portion.

The body can be tubular shaped and comprises one or more radially flexible arms that flexibly engage the spring-biased plunger rod when the control member is in an initial state. The body can be connected to an end cap that closes off an open distal end of the housing when the device is fully assembled. The flexible arm(s) will flex radially outward when the control member moves as a result of premature activation or during purposeful activation, such as during medicament dose delivery. The control member when in the initial state can directly contact the flexible arm to prevent the arm from flexing radially outwards and out of direct engagement with the engagement member of the plunger rod. In a released state of the control member, relative to the body, one or more recesses on an inside surface of the control member align with the one or more flexible arms of the body. The recesses of the control member allow the arms to flex radially outwards, under a bias of a drive member spring, releasing the spring-biased drive member to expel a medicament of a container.

According to another aspect of the disclosure the control member is rotationally movable around a longitudinal axis of the housing when the control member is in the initial state but is axially fixed relative to the body and housing in both the preassembly and finally assembly of device. The locking member is axially movable in the distal direction relative to the body and relative to the control member during the final assembly of the medicament device. Since the control member is axially fixed, then axial distal movement of the locking member during final assembly will cause the locking member to disengage from the control member.

In one possible embodiment of the present disclosure there is a medicament delivery device having a housing and a delivery member guard slidably positioned within the housing, where the delivery member guard has a longitudinal arm that extends distally and has a distally facing bearing surface. A body is positioned within the housing having a first axial position and a second axial position, both relative to the housing. A control member rotatably positioned on and axially fixed relative to the body, where a distal end has a first mating member. There is also a locking member rotatably fixed relative to and positioned on the body, where a proximal end has a second mating member configured to engage with the first mating member when the locking member is in a locked state. When the body is in the first axial position, the first and second mating members are engaged such that rotation of the control member relative to the tubular portion is prevented. The body is moved to the second axial position when the bearing surface of the delivery member guard engages the locking member causing the locking member to become in an unlocked state such that the first and second mating members are disengaged.

According to another aspect of the disclosure, assembly of the powerpack into the housing can result in an axial proximal movement of the powerpack, which includes the control member, relative to the housing such that one or more key members on the housing operatively engage and axially moves the locking member from the locked state to the unlock state. The key member may be a structural feature of the inside or outside of a distal end of the housing, which structural feature interacts with a surface, directly connected to the locking member, to axially move the locking member from the locked state to the unlocked state. The locking member may have a structural feature that corresponds in shape and size to the key member such when the key member and the locking member structural feature engage, the locking member is in or is moving to the unlocked state. The locking member may also have a mating member, preferably a projection, that corresponds in shape and size to a cooperating mating member located on the control member such when the locking member is in the locked state a lock and key type mating cooperation is formed. The locking member in the unlocked state is axially separated from the mating cooperation with the control member such that rotation of the control member relative to the body and relative to the locking member is allowed.

In yet another possible embodiment, the medicament delivery device of the present disclosure has a body and a control member rotatably positioned on and axially fixed relative to the body. The distal end of the control member has a first mating member. A locking member is rotatably fixed relative to the body and has a proximal end with a second mating member configured to engage with the first mating member when the locking member is in a locked state such that rotation of the control member relative to the body is prevented. The locking member is movable axially relative to the body to an unlocked state in which the first and second mating members are disengaged such that the control member is free to rotate relative to the body. There is also an arrangement of a detent and protrusion for maintaining the locking member in the locked state until a certain threshold force is applied to the locking member to move the locking member to the unlocked state. Once the locking member is moved to the unlocked state, the arrangement of the detent and protrusion prevent the locking member moving to the locked state.

The mating member of the control member and its cooperation with the locking member may be any kind of mutually engaging structures, such as protrusions, ratchets, ribs, recesses, teeth, slits, etc., which prevent relative rotation between the control member and the locking member in the locked state, but which allow relative rotation between the control member and the locking member in the unlocked state, and which also allows axial separation, or disengagement, of the mating member and the cooperating mating member on the control member. Like or similar engaging structures can be used for the structural feature of the locking member and the key member.

According to another aspect of the disclosure, the body is coaxially arranged with the control member and the spring-biased drive member, where preferably the drive member is located inside the body and the control member is rotatably position around the body. The body may be an elongated tubular sleeve, accommodating at least a distal portion of the spring-biased drive member.

According to another aspect of the disclosure the body is located radially outside the spring-biased drive member and radially inside the control member, and the locking member is located axially next to the control member. As such, the control member may be a tubular sleeve which is rotationally arranged radially outside the body. The locking member may also be tubular, or ring-shaped, and may be axially movable relative to, and next to, the control member. Preferably the locking member is configured to move distally relative to a distal end of the control member.

According to another aspect of the disclosure the locking member maybe arranged on an outside surface of the body or on an inside surface of the housing such the locking member is rotationally fixed relative to the housing and the body.

According to another aspect of the disclosure, a medicament delivery device comprises a transport lock assembly according to any of the foregoing aspects of the disclosure.

Yet another aspect of the present disclosure includes a method of assembling a medicament delivery device a housing having an open distal end, an open proximal end an inner surface comprising a first fastener is provided. A body having a tubular portion having a detent on an outer surface, an end cap portion, and a second fastener configured to engage the first fastener is separately used to prepare a sub-assembly where a locking member is slid along the tubular portion until a radially projecting protrusion engages the detent such that the locking member is axially fixed relative to the body. A control member having a slot is placed onto the tubular portion such that the slot and projection engage, and the control member becomes rotationally fixed relative to the body. A drive member and drive spring is then inserted into the tubular portion until a recess on an outer surface of the drive member engages with a flexible holding member that is prevented from flexing radially outward by an inner surface of the control member. Finally, the preassembled sub-assembly is inserted into the open distal end of the housing to cause the locking member to move distally disengaging the slot and projection and causing the first fastener to engage with the second fastener.

The above method of assembly can further involve the insertion of the sub-assembly into the housing to cause a key member on an inner surface of the housing to engage with a radially projecting ledge on the locking member to move the locking member from a locked state to an unlocked state. In alternative assembly process, the insertion of the sub-assembly into the housing causes a distally facing bearing surface on a delivery member guard positioned within the housing to engage proximally facing ridge on the locking member to move the locking member from a locked state to an unlocked state.

Yet another aspect of the present disclosure includes a medicament delivery device comprising: a housing having an open terminal distal end and an inner surface comprising a first fastener and a key member; a body comprising a tubular portion, an end cap portion, and a second fastener configured to engage the first fastener, where the body has a first axial position and a second axial position, both relative to the terminal distal end of the housing; a control member rotatably positioned on and axially fixed relative to the tubular portion of the body, where a distal end comprises a slot; a locking member rotatably fixed relative to the housing and positioned on the body, where a proximal end comprises a projection configured to engage with the slot when the locking member is in a locked state, wherein when the body is in the first axial position, the slot and projection are engaged such that rotation of the control member relative to the tubular portion and housing is prevented, and wherein when the body is moved to the second axial position, the first and second fasteners become engaged, the slot and projection disengage, and the locking member is in an unlocked state. According to another aspect of the disclosure, movement of the body from the first position to the second position causes the locking member to engage the key member. According to another aspect of the disclosure, engagement of the key member with the locking member causes the locking member to move axially in a distal direction relative to the body. According to another aspect of the disclosure, the locking member further comprises an outside surface that cooperates with the key member to cause the locking member to move from the locked to the unlocked state as the body moves from the first axial position to the second axial position. According to another aspect of the disclosure, movement of the body from the first axial position to the second axial position causes the first and second fasteners to engage to secure the cap portion to the housing such that the body is axially and rotationally fixed relative to the housing. According to another aspect of the disclosure, the locking member further comprises outwardly directed tabs that engage corresponding cut-outs in the terminal distal end of the housing when the body is in the second axial position. According to another aspect of the disclosure, the body further comprises a detent on an outer surface that releasably axially fixes the locking member relative to body when the locking member is in the locked state. According to another aspect of the disclosure, the medicament delivery device further comprises a delivery member guard, a hollow drive member positioned inside the tubular portion, and a spring that is partially positioned inside of the drive member.

Yet another aspect of the present disclosure includes a medicament delivery device comprising: a housing having an open terminal distal end and an inner surface comprising a first fastener; a delivery member guard slidably positioned within the housing, where the delivery member guard comprises a longitudinal arm extending distally and terminating in a bearing surface; a body comprising a tubular portion, an end cap portion, and a second fastener configured to engage the first fastener, where the body has a first axial position and a second axial position, both relative to the terminal distal end of the housing; a control member rotatably positioned on and axially fixed relative to the tubular portion of the body, where a distal end comprises a slot; a locking member rotatably fixed relative to the housing and positioned on the body, where a proximal end comprises a projection configured to engage with the slot when the locking member is in a locked state, wherein when the body is in the first axial position, the slot and projection are engaged such that rotation of the control member relative to the tubular portion and housing is prevented, and wherein the body is moved to the second axial position when the bearing surface engages the locking member causing the locking member to move to an unlocked state where the slot and projection are disengaged. According to another aspect of the disclosure, movement of the body from the first axial position to the second axial position causes the locking member to slide axially in a distal direction relative to the body. According to another aspect of the disclosure, the body further comprises a detent on an outer surface that releasably axially fixes the locking member relative to body when the locking member is in the locked state. According to another aspect of the disclosure, the medicament delivery device further comprises a hollow drive member positioned inside the tubular portion and a spring that is partially positioned inside of the drive member.

Yet another aspect of the present disclosure includes a method of assembling a medicament delivery device comprising: providing a housing having an open distal end and an open proximal end, where the housing has an inner surface comprising a first fastener; providing a body comprising a tubular portion having a detent on an outer surface, an end cap portion, and a second fastener configured to engage the first fastener; preassembling a sub-assembly comprising: sliding a locking member comprising a proximally projecting projection and a radially projecting protrusion distally along the tubular portion until the protrusion engages the detent such that the locking member is axially fixed relative to the body;

sliding a control member comprising a slot onto the tubular portion such that the slot and projection engage and the control member becomes rotationally fixed relative to the body; inserting a drive member and drive spring into the tubular portion until a recess on an outer surface of the drive member engages with a flexible holding member and where an inner surface of control member prevents the holding member from flexing radially outward and disengaging from the recess, inserting and sliding the sub-assembly into the open distal end of the housing to cause the locking member to move distally disengaging the slot and projection and causing the first fastener to engage with the second fastener. According to another aspect of the disclosure, the insertion of the sub-assembly into the housing causes a key member on an inner surface of the housing to engage with a radially projecting ledge on the locking member to move the locking member from a locked state to an unlocked state. According to another aspect of the disclosure, the insertion of the sub-assembly into the housing causes a distally facing bearing surface on a delivery member guard positioned within the housing to engage a proximally facing ridge on the locking member such that the locking member is moved from a locked state to an unlocked state.

DETAILED DESCRIPTION

Figure 1:
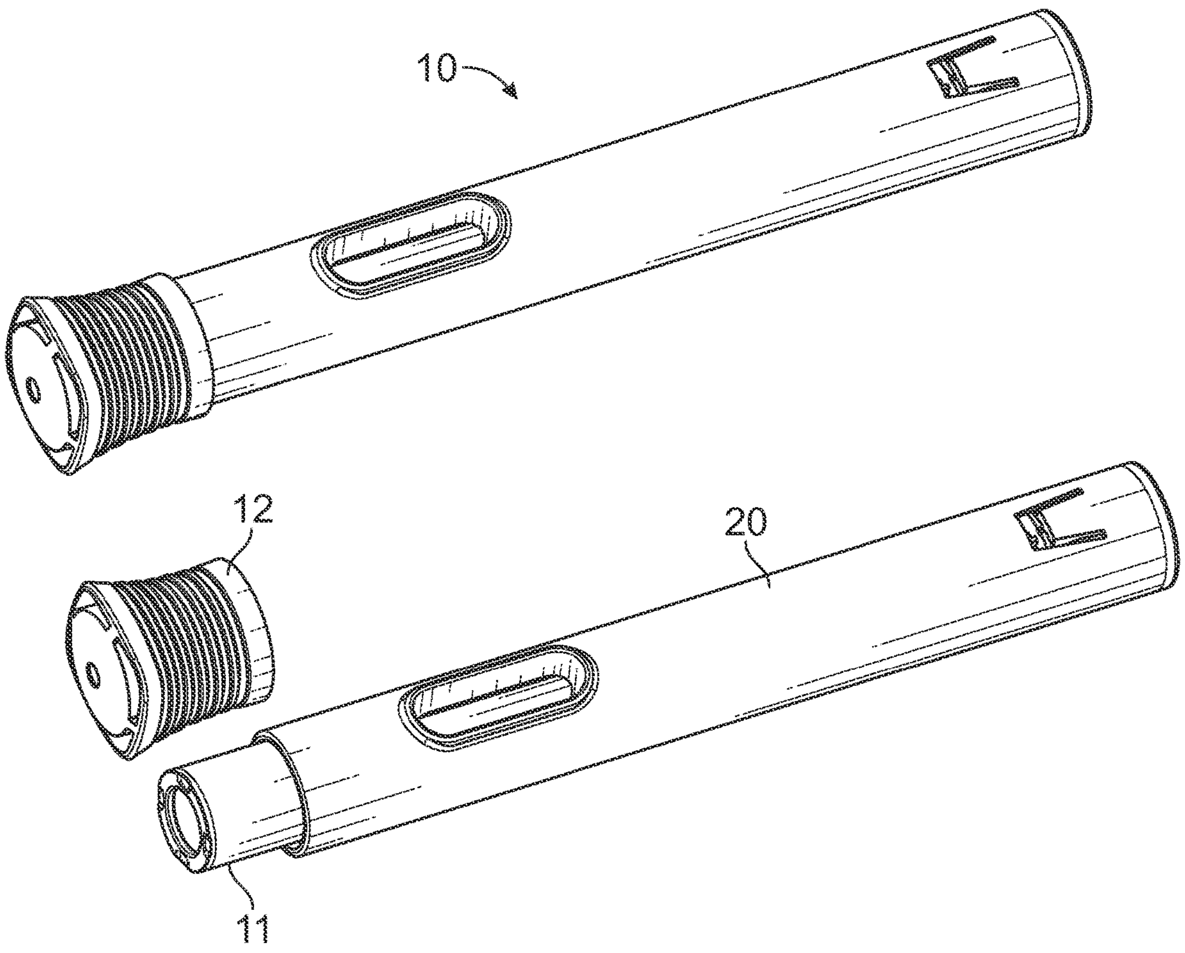
FIG. 1 shows perspective views of one possible medicament delivery device according to the present disclosure with a cap fitted and with the cap removed.

FIG. 1 shows one possible fully assembled embodiment of a medicament delivery device 10 containing one possible transport lock mechanism of the present disclosure and having a removable protective cap 12 attached to the proximal end of housing part or housing 20. A medicament delivery member guard or needle guard 11 is slidably positioned within housing 20 and extends proximally from the terminal proximal end of the housing when the cap 12 is removed.

Figure 2:
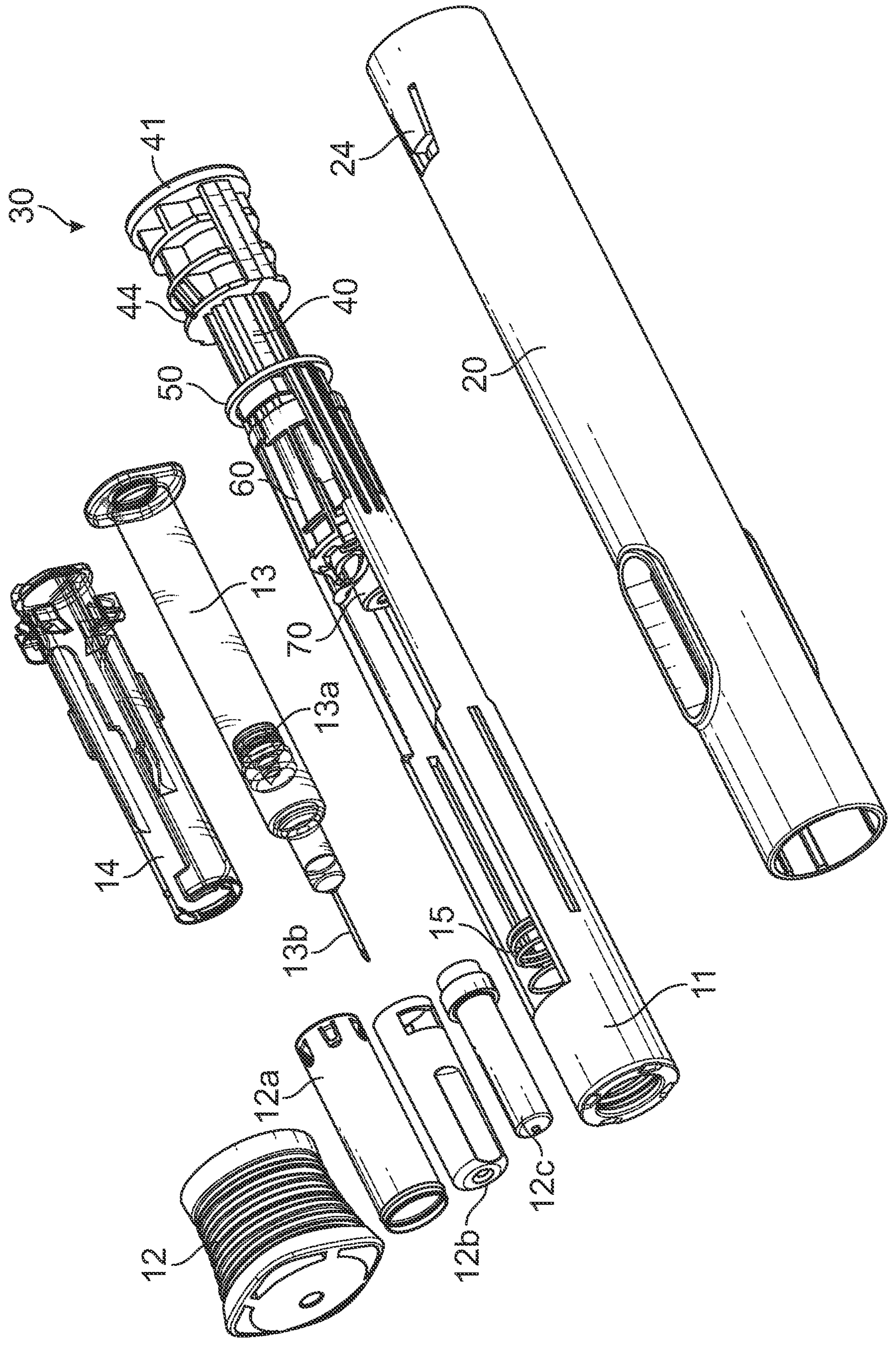
FIG. 2 shows an exploded view of medicament delivery device of FIG. 1.

FIG. 2 shows an exploded view of the delivery device 10 of FIG. 1. A power pack 30 includes a drive member 70 that is initially in a pre-tensioned state and held axially fixed relative to tubular body 40. A control member 60 is rotatably positioned on the tubular body 40, which tubular body 40 terminates in an end cap 41 that is configured to irreversibly connect to the distal end of housing 20 through cooperating connectors 44, 24. As indicated in FIG. 1, a proximal end of the needle guard 11 extends in a first position away from the proximal end of the housing 20 a distance sufficient to cover a delivery member, e.g., an injection needle **13*b*, that is attached to a prefilled syringe 13 containing slidable piston 13*a* sealing a distal end of the syringe 13. The needle 13*b* is initially covered by flexible needle shield (FNS) 12*c* that is engaged with rigid needle shield (RNS) 12*b*. (see FIG. 2). Rigid needle shield remover 12*a* is axially fixed to an inside portion of the protective cap 12 such that rotation and axial movement of cap 12 relative to the housing 20 will cause the RNS 12*b* and attached FNS 12*c* to be separated from the needle 13*b* without rotation of the FNS 12*c* relative to the needle 13*b*. Syringe 13 is held and axially fixed inside syringe holder 14**. In certain device configurations, a medicament container can be used instead of a pre-filled syringe and the medicament delivery member may be a mouthpiece or inhalation orifice.

The needle guard 11 is biased in the proximal direction relative to the housing 20 by spring 15. The drive member 70 can be hollow and contain spring 77 that is supported by rod 71 and surrounded by an end of dose indicator 72. The end of dose indicator 72 is configured to move distally such that it strikes an inside surface of body 40 once medicament delivery process is completed. Needle guard 11 has protrusions 11*a* configured to slide axially in guide track 62 located on the outside surface of control member 60. Legs 11*b* extend distally terminating in bearing surfaces 11*c*.

Figure 3:
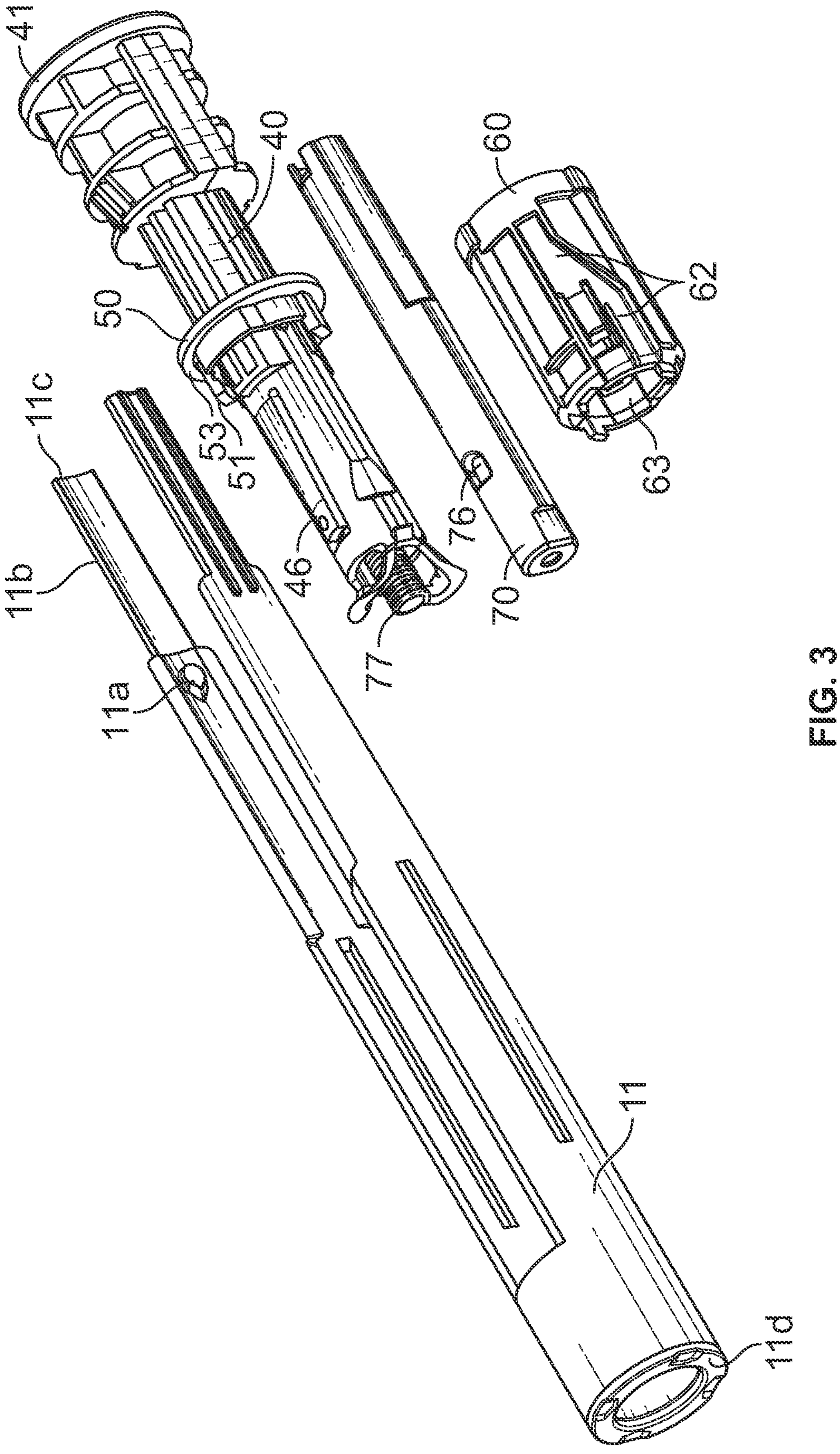
FIG. 3 shows an exploded view of selected components of the medicament delivery device of FIG. 1.
Figure 4:
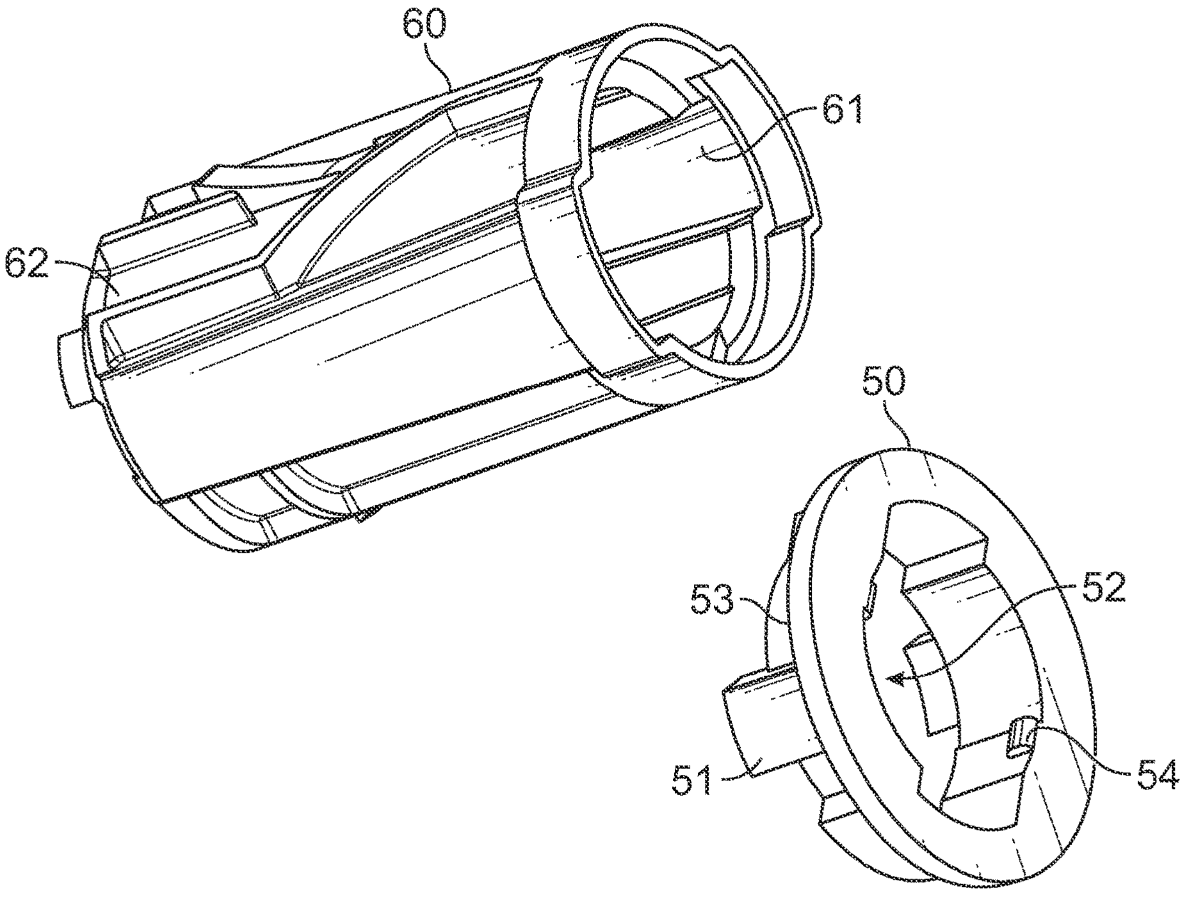
FIG. 4 shows close up views of a control member and a locking member of the medicament delivery device of FIG. 1.

FIG. 3 shows a further exploded view of the powerpack 30 containing one embodiment of locking member 50 slidably positioned on tubular body 40. The locking member 50 may be an annular or tubular member arranged around the body 40 and having a central through hole 52 with one or more mating members, shown as projections 51 (see FIG. 4). Projections 51 are configured to engage and fit within one or more cooperating mating members, shown as slot 61 located on an inside distal portion of the control member 60. A proximally facing ridge 53 is configured to engage with bearing surfaces 11*c* when the needle guard 11 is moved distally relative to the body 40 and housing 20 when the terminal proximal end 11*d* is pressed (pushed) against a medicament delivery (injection) site. In the fully assembled state of the delivery device 10, distal sliding movement of the needle guard 11 in a distal direction will cause protrusions 11*a* to slide within guide tracks 62 and will cause control member 60 to rotate relative to body 40 and housing 20. Such rotation will allow a flexible finger 46 of the body 40 to flex radially outward and release from a holding member, shown as a recess 76, located on the outer surface of drive member 70. The engagement of recess 76 with the flexible finger 46 axially fixes the drive member 70 in a pre-tensioned state relative to body 40 and housing 20 prior to activation of delivery device, i.e., before the process of medicament delivery is purposely started by a user of the device.

Figure 5:
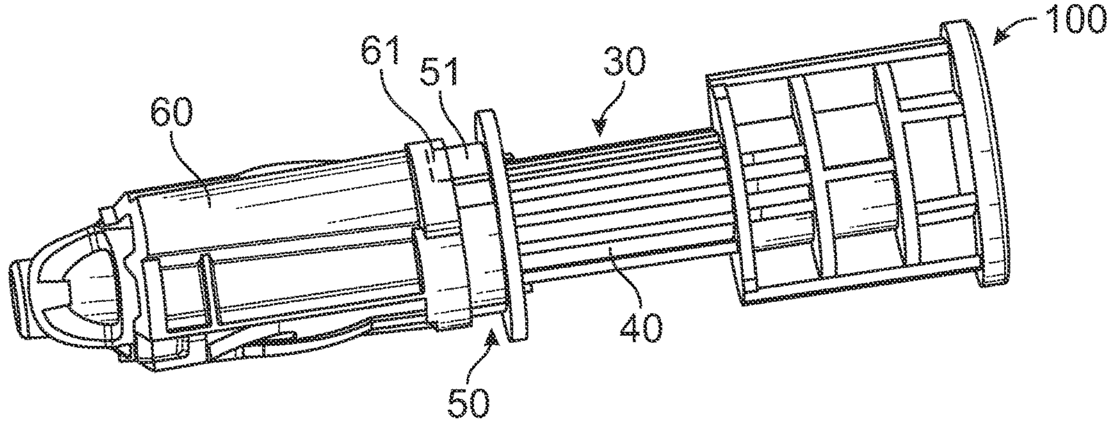
FIG. 5 shows a perspective and cross-sectional view of a powerpack and the locking member, where the locking member is in a locked state.
Figure 5:
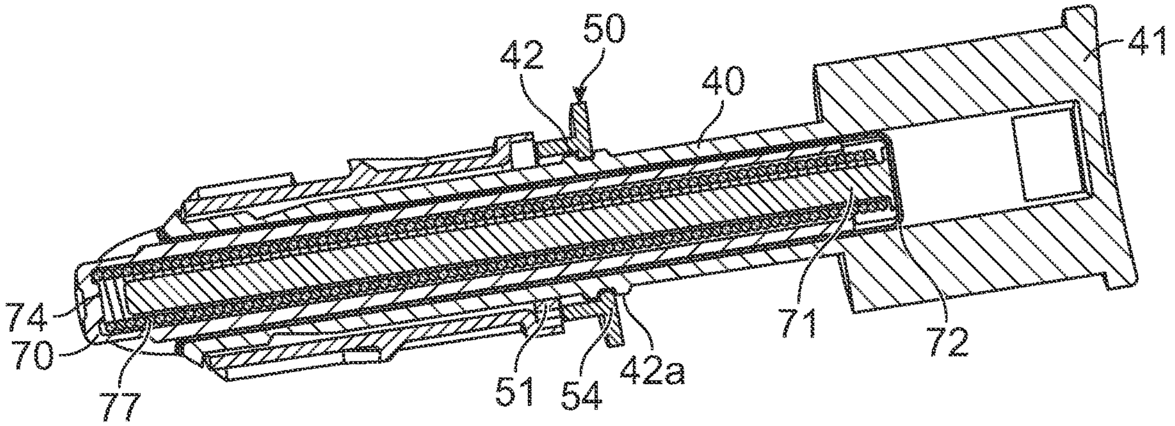

FIG. 5 illustrates the power pack 30 and the locking member 50 as a sub-assembly 100 before the delivery device 10 is fully assembled, i.e., in the unassembled state. Stated differently, the illustrated sub-assembly 100 has not yet been introduced (inserted) into the open distal end of housing 20. It is noted that sub-assembly 100 is just one of a number of the constituent mechanical parts of the medicament delivery device 10 that can be partially prefabricated, pre-assembled, transported and then delivered as individual sub-assemblies or as individual components to a manufacturing or assembly site where the final assembly of device is carried out. Final assembly means the process of assembling the sub-assemblies and/or individual components together with the pre-filled medicament container, shown as syringe 13, at an assembly site.

Preparation of sub-assembly 100 results in the locking member 50 being in the locked state, where control member 60 is immobilized by direct engagement with the locking member 50. As shown in FIG. 5, the powerpack 30 comprises a spring-biased drive member 70, e.g., a plunger rod, that is directly engaged with pre-tensioned spring 77, a body 40 for holding the spring-biased drive member 70 in a pre-tensioned state, a movable control member 60 for releasing the spring-biased drive member 70, and a locking member 50, configured to operatively interact with the control member 60, where locking member 50 is movable relative to the control member 60, from a locked state in which the control member 60 is immobilized, to an unlocked state in which the control member 60 is free to move, e.g., rotate. Compression spring 77 can be pre-tensioned between a proximal inner surface 74 of the drive member 70 and a proximally facing surface of the end of dose indicator 72, shown as a U-shape bracket in FIG. 5. Upon completion of the medicament delivery, the distal end of spring 77 will push the end of dose indicator 72 distally until the distally facing surface strikes an inside surface of body 40 at the end cap 41.

The body 40 may be generally tubular, and may comprise a radially flexible holding member or flexible finger 46, such as a flexible arm having an inward protrusion, which engages a corresponding holding member 76, e.g., a recess, located on an outer surface of the spring-biased drive member 70, in order to hold the spring-biased drive member 70 in the pre-tensioned state. The drive member 70 is coaxial with the body 40 and is located radially inside the body 40. The control member 60 may be tubular and is coaxial with the body 40 and is further located radially outside the body 40. An inner surface of the control member 60 abuts the holding member 46 such that it is prevented from flexing radially outwards under the bias of the spring 77 when the control member 60 is in an initial state.

If the control member 60 is moved to a released state, such as by interaction with the medicament delivery member guard 11, a recess 63 or recesses on the inside surface of the control member 60 will move such that it/they will align radially with the holding member 46. This alignment allows the inwardly biased/held flexible holding member 46 to flex radially outwards into the recesses 63. This flexing outward of holding member 46 is caused by the proximally directed force exerted by drive spring 77 that biases the spring-biased drive member 70 forward in the proximal direction. This spring force causes the holding member 46 to be forced outwards out of the corresponding holding member, e.g., recess 76. When the holding member 46 is disengaged from the recess 76, the spring-biased drive member 70 will move proximally. If the medicament delivery device 10 is completely assembled, the spring-biased drive member 70 will be in abutment with sliding piston 13*a* in the medicament container, e.g., syringe 13, and will consequently drive/slide the piston 13*a* forward, proximally, to expel a medicament through the medicament delivery member, e.g., needle 13*b*.

If, on the other hand, the control member 60 is somehow, e.g. by accident, moved to the released state before the medicament delivery device 10 is completely assembled, the spring-biased drive member 70 will be catapulted (shot) out of the powerpack 30, which may be harmful to a person handling the device. In addition, the powerpack 30 will be expended and wasted by such a premature activation. In order to mitigate the problem of accidental activation of the powerpack 30, the present disclosure incorporates the locking member 50 to releasably engage the control member 60 to prevent premature movement of control member 60, e.g., by rotation, from the initial non-activated state to the released, activated state.

In the exemplified embodiments of the present disclosure, the locking member 50 is provided to prevent the control member 60 from moving relative to the body 40 and housing 20. In particular, when the control member 60 is configured to be rotationally movable around a longitudinal axis of the housing 20, and axially fixed relative to the body 40, the locking member 50 is configured to releasably engage the control member 60. Preferably, the locking member 50 is axially movable, but rotationally locked, relative to the body 40, and relative to the control member 60. The locking member 50 is configured to interact with the control member 60, such that when the locking member 50 is in the locked state, the control member 60 is immobilized by the locking member 50. When the locking member 50 is moved to the unlocked state, the control member 60 and the locking member 50 are then disengaged from each other because the locking member 50 has moved axially in the distal direction away from the control member 60. Accordingly, it is preferred that the locking member 50 may be slidably positioned axially next to the control member 60 so that it can be pushed distally away from engagement with the control member 60 during a final assembly process.

FIG. 5 shows the physical relationship of the locking member 50 with the powerpack 30 when in the locked state when the sub-assembly 100 is pre-fabricated and before the final assembly of device 10. The locking member 50 is slidably positioned on body 40 such that projection 51 is axially positioned within and engaged with slot 61 on the inside of control member 60. This engagement between the slot 61 and projection 51 prevents the control member 60 from rotating because the locking member 50 is rotationally fixed relative to the body 40. The locking member 50 is held in the locked state by the interaction of protrusion 54 with detent 42 formed on the outside surface of body 40. This interaction works to temporarily axially fix the locking member 50 relative to the body 40 while sub-assembly is assembled, packaged, transported, and eventually assembled into housing 20. This temporary/releasable engagement of the detent 42 with protrusion 54 ensures that the projection 51 remains in slot 61, thus preventing movement of the control member 60.

Figure 6:
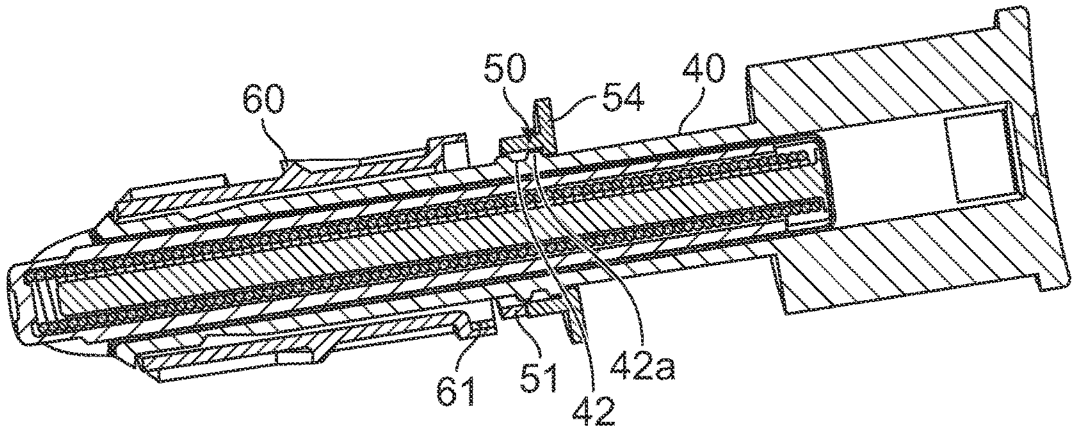
FIG. 6 shows a cross-sectional view of the powerpack and locking member of FIG. 5, where the locking member is in an unlocked state.
Figure 7:
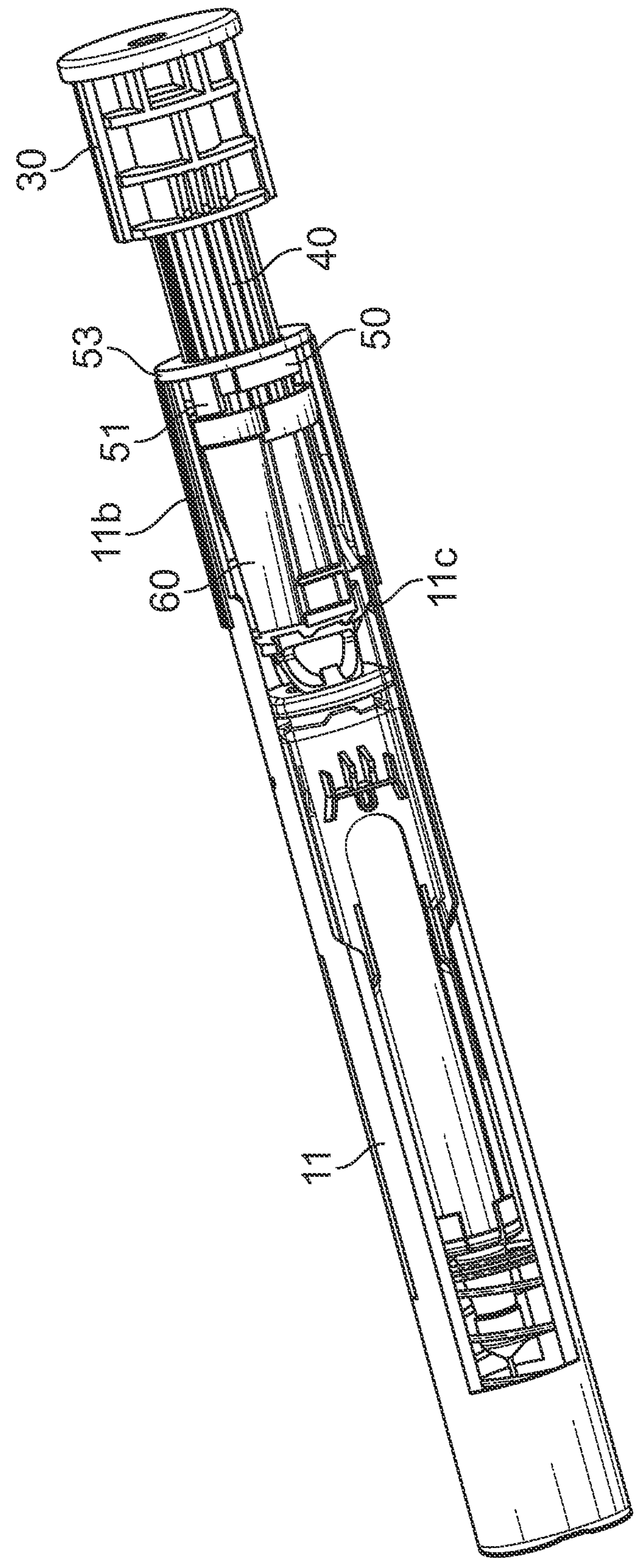
FIG. 7 shows a partially disassembled view of the powerpack and locking member of FIG. 5 where the delivery member guard abuts the locking member that is in an unlocked state.
Figure 8:
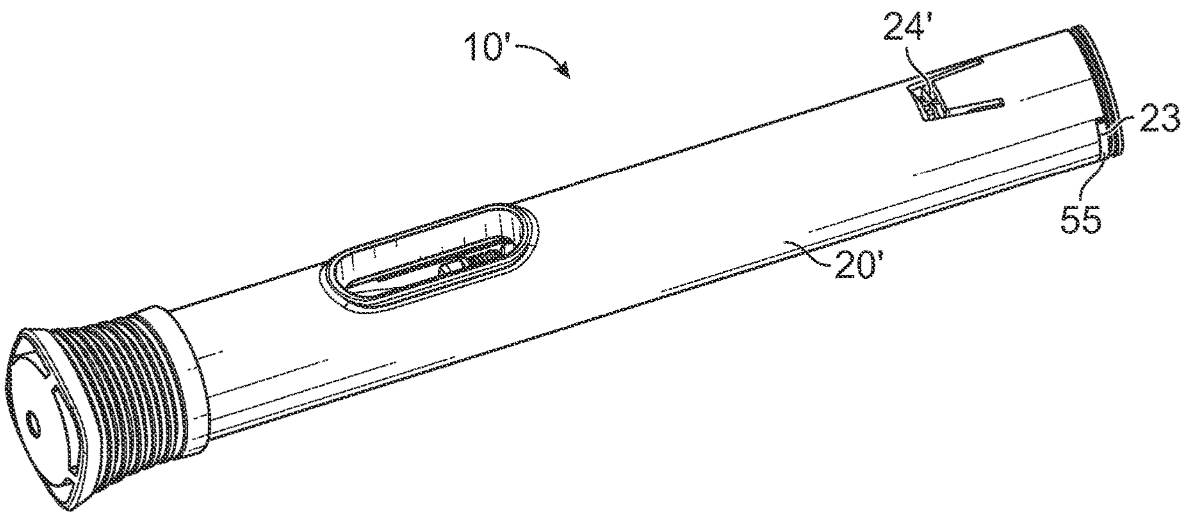
FIG. 8 shows a perspective view of another possible medicament delivery device according to the present disclosure.

During the final assembly process of the medicament delivery device 10, the locking member 50 is axially moved (pushed) distally such that the protrusion 54 disengages from detent 42, which in turn disengages projection 51 from slot 61 (see FIG. 6). The proximal end 42*a* of detent 42 is configured as a hard stop for protrusion 54, thus preventing locking member 50 from shifting or moving axially proximally. After final assembly of the device 10, the locking member 50 will remain in the unlocked state with protrusion 54 being located distal to the detent 42. Axial movement of the locking member 50 during final assembly results from engagement of bearing surfaces 11*c*, which are located on the terminal distal ends of legs 11*b* of needle guard 11, with the proximally facing ridge 53 of locking member 50. During final assembly of the delivery device 10, preferably the powerpack 30 with locking member 50 in the locked state, i.e., sub-assembly 100, is inserted into the open distal end of housing 20 and then securely attached through irreversible snap locks 24, 44, screw threads, adhesive, welding, or the like permanent connections. Once the sub-assembly 100 is locked into housing 20, then needle guard 11, e.g., as part another sub-assembly, is inserted into the open proximal end of housing 20. As the needle guard 11 is slid distally relative to the housing 20, the bearing surfaces 11*c* of needle guard 11 will eventually come into contact with ridge 53 and will push locking member 50 distally relative to control member 60 and body 40. This is because both the control member 60 and body 40 are axially fixed relative to the housing 20. As the needle guard 11 is inserted further into housing 20 the legs 11*b* will push the locking member 50 so that it transitions from the locked state to the unlocked state and will cause the projection 51 to disengage from slot 61. (see FIG. 7). As the projection 51 disengages from slot 61, the protrusions 11*a* will become positioned into guide tracks 62. This will then prevent the control member 60 from rotating because the needle guard 11 is rotationally fixed relative to the housing 20.

Towards the end of the insertion of sub assembly 100 into the distal end of the housing 20, fastening elements 44 on the body 40 will engage with corresponding fastening elements 24 of the housing 20 to form an irreversible snap-fit engagement, such that the body 40, and consequently the powerpack 30, and the housing 20 are locked to each other.

During activation of the fully assembled delivery device 10 to administer the medicament, the terminal proximal end of the needle guard 11 is pushed against a delivery (injection) site. This causes the protrusions 11*a* to move distally along guide tracks 62. Since the guide tracks 62 are not linear and the needle guard 11 cannot rotate, then the control member 60 will rotate as the protrusions move along the track or tracks 62 in the distal direction. The rotation of the control member 60 will move an inside surface of the control member 60 out of engagement with the flexible holding member 46 allowing it to flex radially outward and release from the drive member recess 76 and into cut-out 63 on the inside surface of the control member 60. The pre-tensioned spring 77 will then urge drive member 70 forward in the proximal direction causing expulsion of the medicament in syringe 13 through needle 13*b*.

Figure 11:
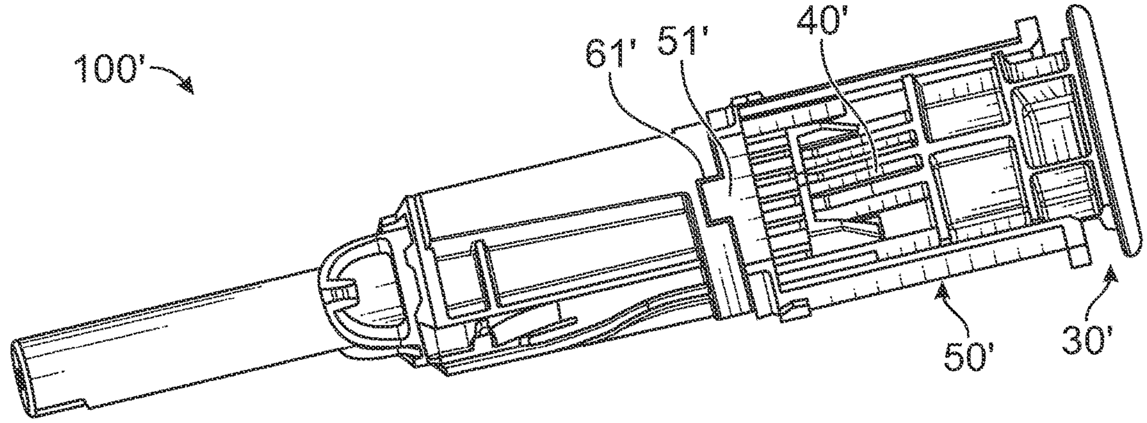
FIG. 11 shows a perspective and cross-sectional view of the powerpack and the locking member of the medicament delivery device of FIG. 8, where the locking member is in a locked state.
Figure 11:
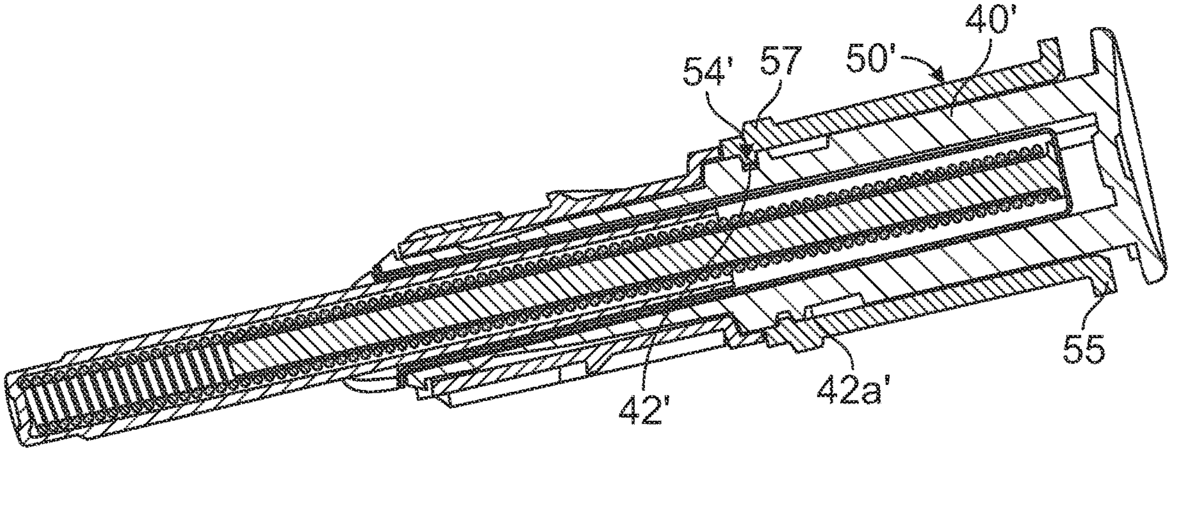
Figure 12:
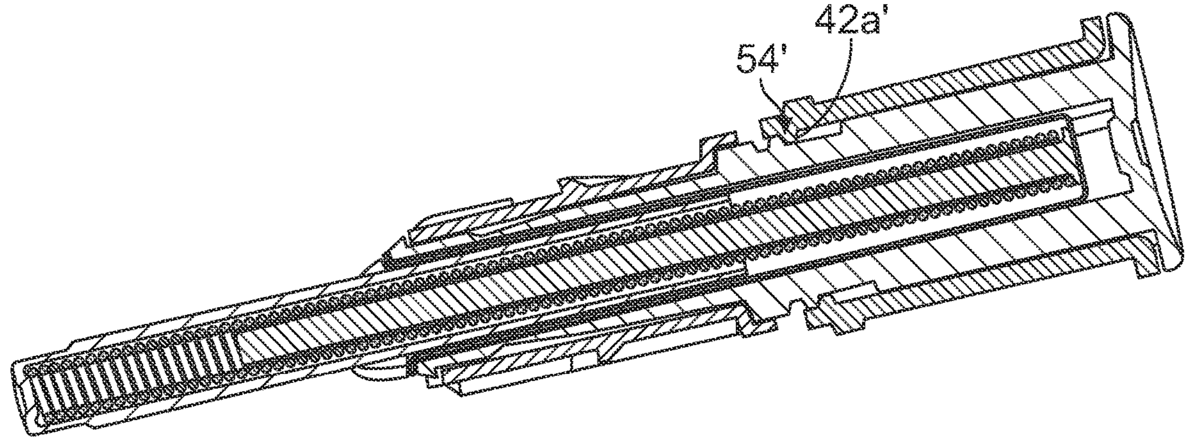
FIG. 12 shows a cross-sectional view of the powerpack and locking member of FIG. 11, where the locking member is in an unlocked state.
Figure 13:
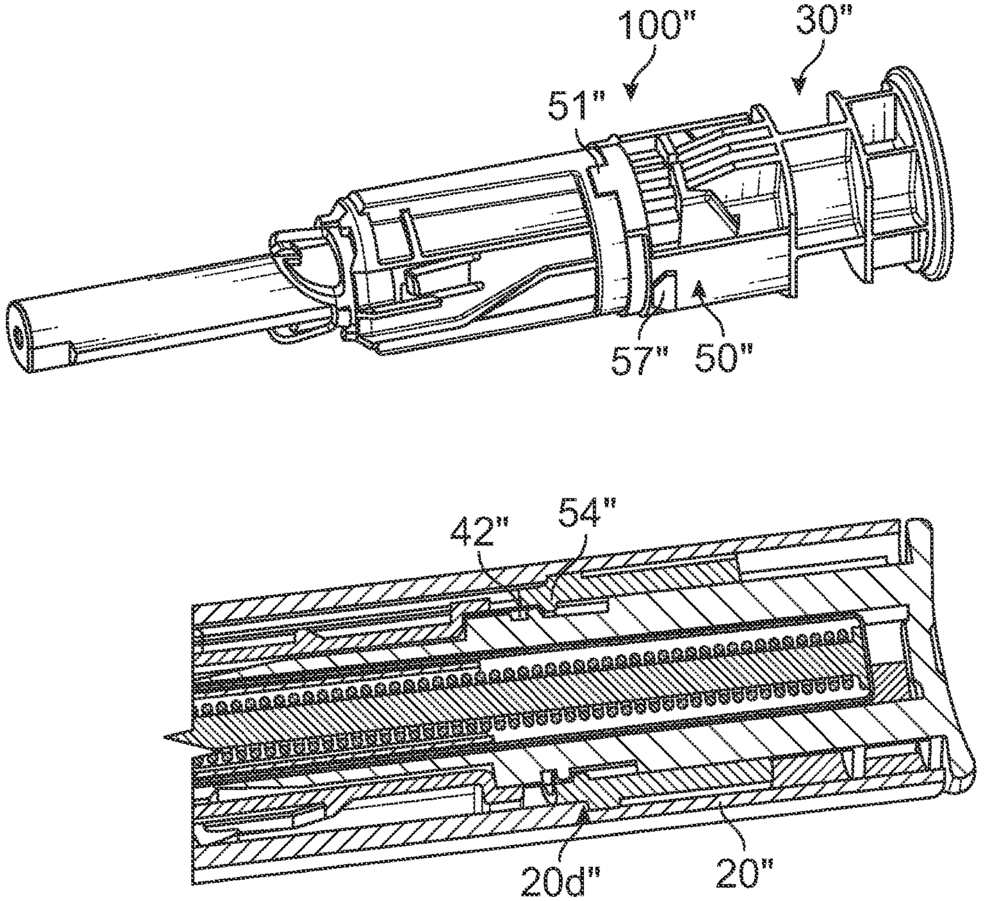
FIG. 13 shows a perspective and cross-sectional view of another possible embodiment of the powerpack and locking member in a locked and unlocked state.

FIGS. 9-13 present another embodiment of the transport lock assembly of the present disclosure. In contrast to the above-described transport lock assembly embodiment that uses the needle guard 11 to move the locking member from a locked to an unlocked state, the below described embodiments use an interaction between the housing and the locking member to cause the locking member to disengage from the control member. Two possible locking member configurations are shown in FIGS. 9-13. The first configuration is illustrated in FIGS. 9-12. The other "hidden" locking member configuration is shown in FIG. 13.

Figure 9:
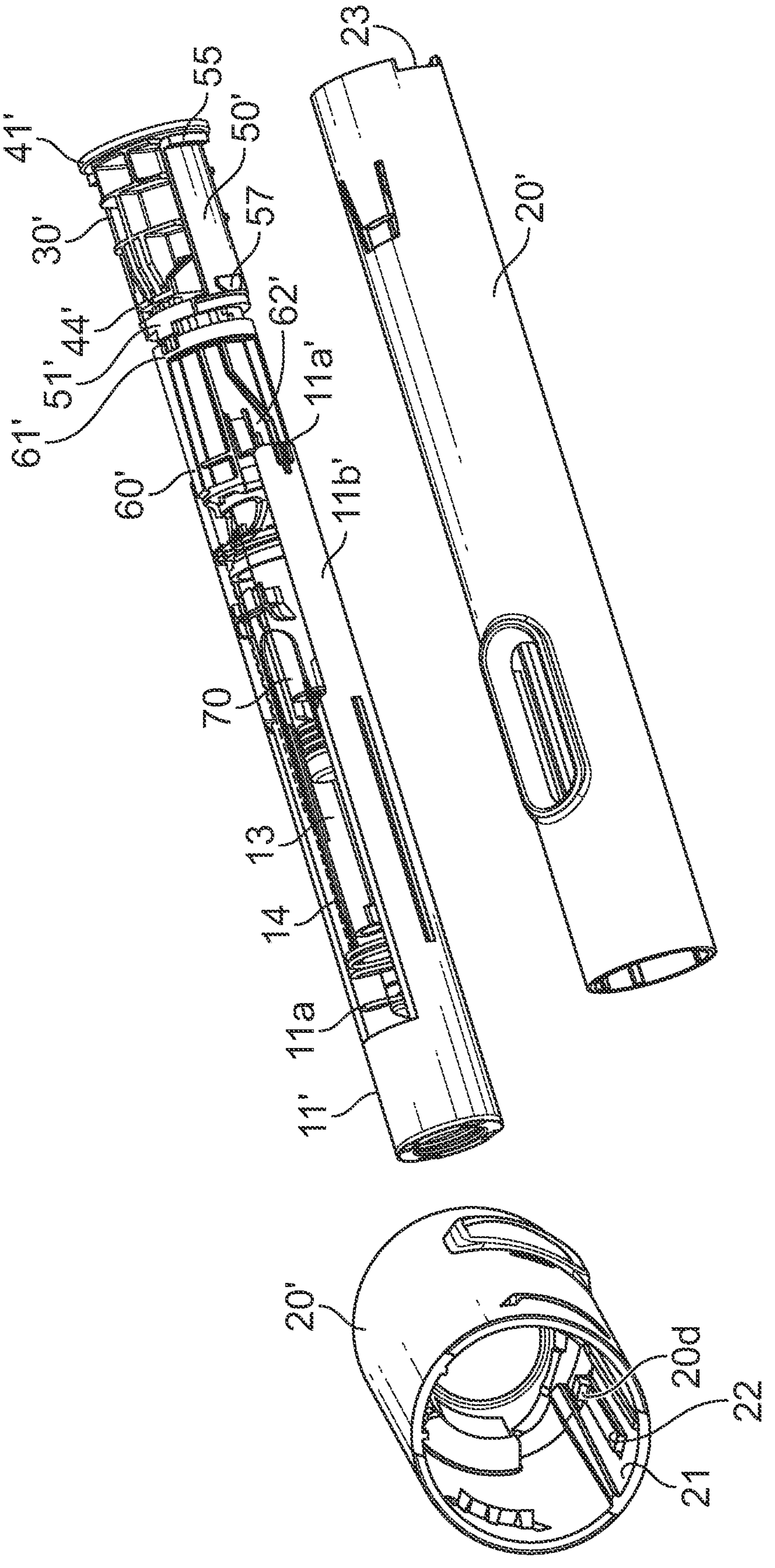
FIG. 9 shows a partial exploded view of medicament delivery device of FIG. 8 and an inside view of the housing.
Figure 10:
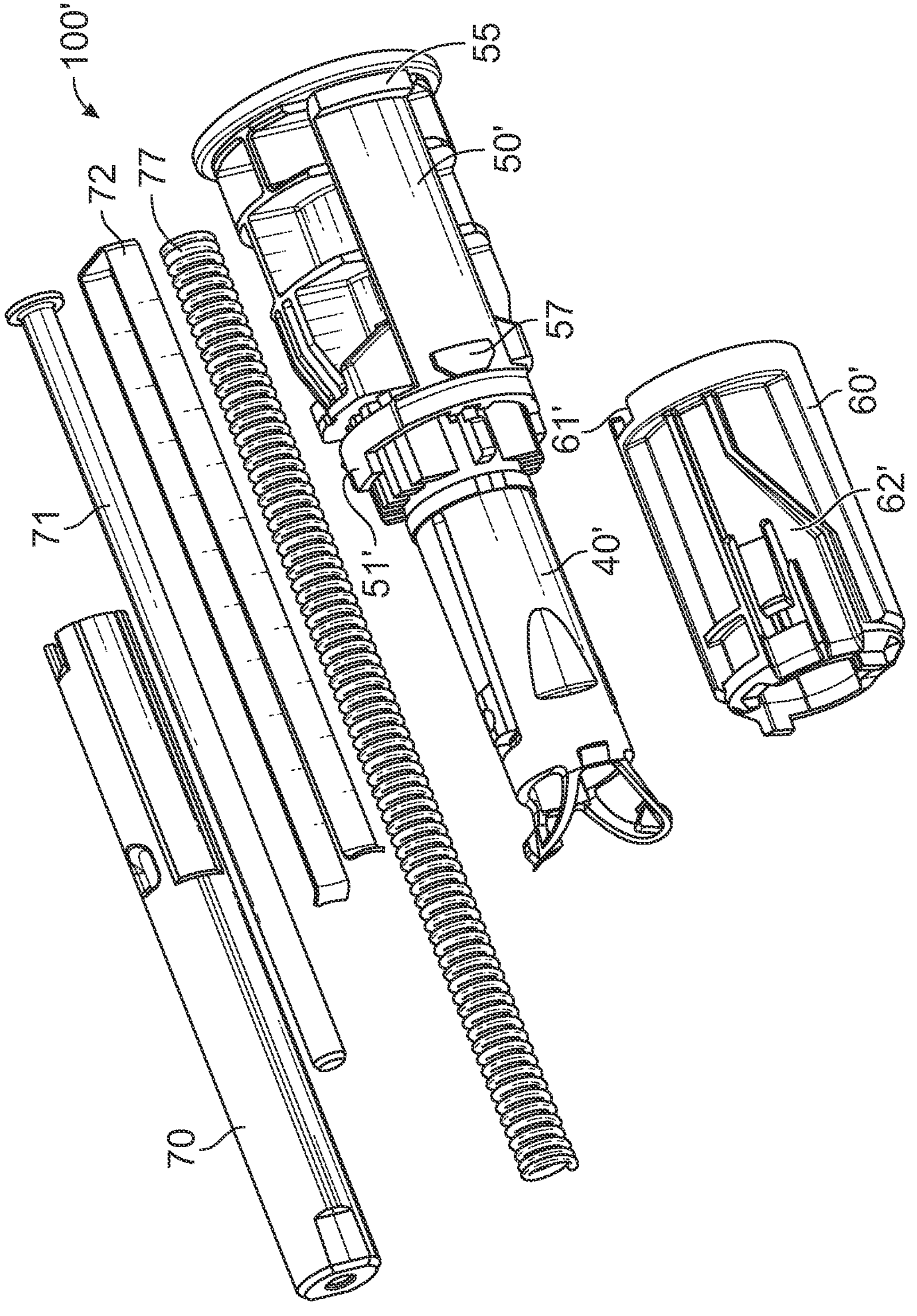
FIG. 10 shows an exploded view of a powerpack and a locking member of the medicament delivery device of FIG. 8.

As indicated above, the housing 20', 20" is configured to receive the powerpack 30". An inside portion of the housing 20', 20" comprises a key member 22 located in longitudinal guide 21 (see FIG. 9). This guide 21 is configured to cooperate with arms 11*a'* that extend proximally on needle guard 11' to guide the needle guard 11' during the assembly process and to prevent rotation of the needle guard 11' relative to the housing 20'. FIGS. 9 and 10 show the locking member 50' in the unlocked state where the key member 22 has abutted an outward radially directed wedge or ledge 57 during insertion of the power pack 30' into the open distal end of the housing 20'.

During assembly of the delivery device 10' as the power pack slides relative to the housing 20', the key member 22 engages the wedge 57 on the locking member 50' causing the locking member 50' to slide distally until a projection or projections 51' disengage from a slot or slots (cut-out or cut-outs) 61' at the terminal distal end of control member 60'. Once the powerpack and locking member 50' are completely assembled into housing 20' the tabs 55 will fit into corresponding cut-outs 23 at the terminal distal end of the housing 20'. These tabs 55 are configured as support ribs during movement of the locking member 50' such that the ribs interact with the housing 20' during the final assembly of the delivery device 10'. As with the above-described embodiment, once the locking member 50' moves to the unlocked state, the protrusions 11*a'* will be positioned within guide tracks 62', which will prevent rotation of the needle guard 11' relative the housing 20' and the body 40'.

FIG. 11 shows the power pack 30' and the locking member 50', i.e., sub-assembly 100', where the locking member 50' is in the locked state such that projection 51' is positioned within cut-out 61' to prevent premature rotation of the control member 60' prior to the final assembly of delivery device 10'. Cooperation of a detent 42' and protrusion 54' is used to maintain the axial alignment of the projections 51' into cut-outs 61' until insertion of the sub-assembly 100' into the open distal end of the housing 20'. On application of a certain threshold force the engagement of the key member 22 with wedge 57 causes the locking member to move to the unlocked state and the protrusion 54', as shown in FIG. 12, will have moved out of the detent 42' and will be positioned distally of the detent.

A variation of the above just described embodiment uses a so-called "hidden" locking member 50" (see FIG. 13) that does not have tabs 55 that cooperate with housing cut-outs 23. Instead, the axially sliding locking member 50" is completely contained (not visible) within the housing 20" both in the locked and unlocked state. As previously described, as the sub-assembly 100" is inserted into the housing 20" during a final assembly process, the wedge 57" will engage the key member 22 causing the locking member to slide distally relative to body 40' to move the locking member 50" from the locked state to the unlocked state. The key member 22 may include a distally directed ledge **20*d* provided at a proximal end of the longitudinal guide 21. The wedge 57, 57" of the locking member 50', 50" may be configured as a guide follower such that the wedge slides along the guide 21 when inserting the powerpack 30', 30" into the housing 20', 20". Alternatively, the key member 22** may be configured as a structural feature, e.g., a ledge, or a protrusion, that is formed of any of the other components or sub-assemblies that are used to fabricate the final assembled delivery device.

As in the other embodiment previously described, towards the end of the insertion of sub assembly 100', 100" into the distal end of the housing, fastening elements 44' on the body will engage with corresponding fastening elements 24' of the housing 20' to form an irreversible snap-fit engagement, such that the body 40', and consequently the powerpack 30', and the housing part 20', 20" are locked to each other.

The invention claimed is:

1. A medicament delivery device comprising:

a housing having an open terminal distal end with a distally facing surface;

a body locatable in the housing and having a first axial position and a second axial position, both relative to the terminal distal end of the housing;

a control member rotatably positioned on and axially fixed relative to the body, where a distal end comprises a first mating member;

a locking member rotatably fixed relative to the body, where a proximal end comprises a second mating member configured to engage with the first mating member when the locking member is in a locked state, and where a distal end comprises a tab, wherein engagement of the distally facing surface with the locking member causes the locking member to move axially in a distal direction relative to the body, wherein when the body is in the first axial position, the first and second mating members are engaged such that rotation of the control member relative to the body is prevented, wherein when the body is moved to the second axial position, the tab engages with the distally facing surface of the housing to cause the first and second mating members to disengage and the locking member to be in an unlocked state in which the control member is free to rotate relative to the body.

2. The medicament delivery device of claim 1, wherein movement of the body from the first axial position to the second axial position causes the locking member to engage the distally facing surface.

3. The medicament delivery device of claim 1, wherein the locking member further comprises an outside surface that cooperates with the distally facing surface to cause the locking member to move from the locked state to the unlocked state as the body moves from the first axial position to the second axial position.

4. The medicament delivery device of claim 1, wherein movement of the body from the first axial position to the second axial position causes a fastener on the housing to engage a cooperating fastener on the body to secure a cap portion of the body to the housing such that the body is axially and rotationally fixed relative to the housing.

5. The medicament delivery device of claim 1, wherein the locking member further comprises outwardly directed tabs that engage corresponding cut-outs in a terminal distal end of the housing when the body is in the second axial position.

6. The medicament delivery device of claim 1, wherein the body further comprises a detent on an outer surface that releasably axially fixes the locking member relative to body when the locking member is in the locked state.

7. The medicament delivery device according to claim 1, further comprising:

a delivery member guard;

a hollow drive member positioned inside a tubular portion of the body; and a spring that is partially positioned inside of the hollow drive member.

8. The medicament delivery device according to claim 1, further comprising a delivery member guard comprising a terminal proximal end extending proximally beyond a proximal end of the housing and distally extending arms that are engaged with the control member.

9. The medicament delivery device of claim 8, wherein when the terminal proximal end of the delivery member guard is pushed against an injection site, protrusions on the distally extending arms move distally in guide tracks on an outside surface of the control member and rotates the control member relative to the housing.

10. The medicament delivery device of claim 1, further comprising a hollow drive member axially fixed inside a tubular portion of the body and having a compressed spring that is partially positioned inside of the hollow drive member biasing the hollow drive member proximally, where rotation of the control member releases the hollow drive member from the tubular portion such that the compressed spring decompresses and moves the hollow drive member proximally relative to the housing.

11. A medicament delivery device comprising:

a housing having an open terminal distal end with a distally facing surface;

a body locatable in the housing and having a first axial position and a second axial position, both relative to the terminal distal end of the housing;

a control member rotatably positioned on and axially fixed relative to the body, where a distal end comprises a first mating member;

a locking member rotatably fixed relative to the body, where a proximal end comprises a second mating member configured to engage with the first mating member when the locking member is in a locked state, and where a distal end comprises a tab, wherein the locking member further comprises outwardly directed tabs that engage corresponding cut-outs in a terminal distal end of the housing when the body is in the second axial position, wherein when the body is in the first axial position, the first and second mating members are engaged such that rotation of the control member relative to the body is prevented, wherein when the body is moved to the second axial position, the tab engages with the distally facing surface of the housing to cause the first and second mating members to disengage and the locking member to be in an unlocked state in which the control member is free to rotate relative to the body.

12. The medicament delivery device of claim 11, wherein movement of the body from the first axial position to the second axial position causes the locking member to engage the distally facing surface.

13. The medicament delivery device of claim 11, wherein movement of the body from the first axial position to the second axial position causes a fastener on the housing to engage a cooperating fastener on the body to secure a cap portion of the body to the housing such that the body is axially and rotationally fixed relative to the housing.

14. The medicament delivery device of claim 11, wherein movement of the body from the first axial position to the second axial position causes the locking member to slide axially in a distal direction relative to the body.

15. The medicament delivery device of claim 11, wherein the locking member further comprises an outside surface that cooperates with the distally facing surface to cause the locking member to move from the locked state to the unlocked state as the body moves from the first axial position to the second axial position.

16. The medicament delivery device of claim 11, wherein the body further comprises a detent on an outer surface that releasably axially fixes the locking member relative to body when the locking member is in the locked state.

17. A medicament delivery device comprising:

a housing having an open terminal distal end with a distally facing surface;

a body locatable in the housing and having a first axial position and a second axial position, both relative to the terminal distal end of the housing;

a control member rotatably positioned on and axially fixed relative to the body, where a distal end comprises a first mating member;

a delivery member guard comprising a terminal proximal end extending proximally beyond a proximal end of the housing and distally extending arms that are engaged with the control member, a locking member rotatably fixed relative to the body, where a proximal end comprises a second mating member configured to engage with the first mating member when the locking member is in a locked state, and where a distal end comprises a tab, wherein when the body is in the first axial position, the first and second mating members are engaged such that rotation of the control member relative to the body is prevented, wherein when the body is moved to the second axial position, the tab engages with the distally facing surface of the housing to cause the first and second mating members to disengage and the locking member to be in an unlocked state in which the control member is free to rotate relative to the body.

18. The medicament delivery device of claim 17, wherein when the terminal proximal end of the delivery member guard is pushed against an injection site, protrusions on the distally extending arms move distally in guide tracks on an outside surface of the control member and rotates the control member relative to the housing.

19. The medicament delivery device according to claim 17, further comprising a hollow drive member positioned inside a tubular portion of the body and a spring that is partially positioned inside of the hollow drive member.

20. The medicament delivery device of claim 17, further comprising a hollow drive member axially fixed inside a tubular portion of the body and having a compressed spring that is partially positioned inside of the hollow drive member biasing the hollow drive member proximally, where rotation of the control member releases the hollow drive member from the tubular portion such that the compressed spring decompresses and moves the hollow drive member proximally relative to the housing.

* * * * *